(12) United States Patent
Hjellum

(10) Patent No.: US 9,874,550 B2
(45) Date of Patent: Jan. 23, 2018

(54) METHOD FOR THE QUANTIFICATION OF 227AC IN 223RA COMPOSITIONS

(71) Applicant: BAYER AS, Oslo (NO)

(72) Inventor: Gro Elisabeth Hjellum, Bærums Verk (NO)

(73) Assignee: BAYER AS, Oslo (NO)

( * ) Notice: Subject to any disclaimer, the term of this patent is extended or adjusted under 35 U.S.C. 154(b) by 0 days.

(21) Appl. No.: 14/912,312

(22) PCT Filed: Aug. 13, 2014

(86) PCT No.: PCT/EP2014/002222
§ 371 (c)(1),
(2) Date: Feb. 16, 2016

(87) PCT Pub. No.: WO2015/022074
PCT Pub. Date: Feb. 19, 2015

(65) Prior Publication Data
US 2016/0209387 A1    Jul. 21, 2016

(30) Foreign Application Priority Data
Aug. 16, 2013 (GB) .................................. 1314718.6

(51) Int. Cl.
*G01N 33/15* (2006.01)
*B01D 15/08* (2006.01)
(Continued)

(52) U.S. Cl.
CPC ............. *G01N 33/15* (2013.01); *B01D 15/08* (2013.01); *B01D 15/1871* (2013.01); *C01F 13/00* (2013.01); *G01N 30/00* (2013.01); *G01T 1/36* (2013.01); *G21G 1/001* (2013.01); *G01N 2030/009* (2013.01); *G01N 2030/8868* (2013.01); *G01N 2033/0093* (2013.01); *G21G 2001/0089* (2013.01)

(58) Field of Classification Search
CPC ........... G01N 33/15; G01N 30/00; G01T 1/36
USPC ...................................... 436/57, 81–82, 178
See application file for complete search history.

(56) References Cited

U.S. PATENT DOCUMENTS 5,809,394 A * 9/1998 Bray ....................... C22B 60/00
                                                                                         250/432 PD
5,854,968 A    12/1998 Horwitz et al.
(Continued)

FOREIGN PATENT DOCUMENTS

DE     10 2006 008 023 A1    8/2007

OTHER PUBLICATIONS

Jia, G. et al, Journal of Environmental Radioactivity 2012, 106, 98-119.*

(Continued)

*Primary Examiner* — Arlen Soderquist
(74) *Attorney, Agent, or Firm* — Nixon & Vanderhye P.C.

(57) ABSTRACT

A method for the quantification of $^{227}$Ac in a $^{223}$Ra composition comprising passing the composition through a first solid phase extraction column A, wherein said column comprises a thorium specific resin, passing the eluate of column A through a second solid phase extraction column B, wherein said column comprises an actinium specific resin and recovering the $^{227}$Ac absorbed onto the resin in column B and determining the amount thereof.

18 Claims, 4 Drawing Sheets

Process flow-chart for actinium, thorium and radium separation and purification using the method of the invention - extraction is shown using aqueous HNO₃ of particular concentrations by way of example only.

(51) Int. Cl.
*B01D 15/18* (2006.01)
*C01F 13/00* (2006.01)
*G01N 30/00* (2006.01)
*G01T 1/36* (2006.01)
G01N 30/88 (2006.01)
G21G 1/00 (2006.01)
G01N 33/00 (2006.01)

(56) References Cited

U.S. PATENT DOCUMENTS

| | | | |
|---|---|---|---|
| 6,787,042 B2 * | 9/2004 | Bond | B01J 39/04 |
| | | | 210/143 |
| 2003/0127395 A1 * | 7/2003 | Bond | B01J 39/04 |
| | | | 210/682 |
| 2003/0194364 A1 * | 10/2003 | Bond | G21G 1/0005 |
| | | | 423/2 |
| 2003/0206857 A1 * | 11/2003 | Larsen | A61K 51/1282 |
| | | | 424/1.11 |
| 2004/0166060 A1 * | 8/2004 | Sgouros | A61K 51/1234 |
| | | | 424/1.65 |
| 2007/0163957 A1 * | 7/2007 | Horwitz | B01D 15/3804 |
| | | | 210/638 |
| 2013/0095031 A1 * | 4/2013 | Karlson | A61K 51/1282 |
| | | | 424/1.11 |

OTHER PUBLICATIONS

Dulaiova, H. et al, Journal of radioanalytical and nuclear Chemistry 2013, 296, 279-283.*

Martin et al., "Determination of $^{227}$Ac by alpha-Particle Spectrometry", *Applied Radiation and Isotopes, Elsevier*, Oxford, GB, vol. 46, No. 10 (1995) pp. 1065-1070.

Bojanowski et al., "Determination of 227Ac In Environmental Samples by Ion-Exchange and Alpha Spectrometry", *Journal of Radioanalytical and Nuclear Chemistry, Articles*, vol. 115, No. 1 (1987), pp. 23-37.

Köhler et al., "Simultaneous determination of Ra and Th nuclides, 238U and 227Ac in uranium mining waters by γ-ray spectrometry", *Applied Radiation and Isotopes, Elsevier*, Oxford GB, vol. 52, No. 3 (2000), pp. 717-723.

International Search Report for related PCT Application No. PCT/EP2014/002222 (dated Oct. 8, 2014); 3 pages.

* cited by examiner

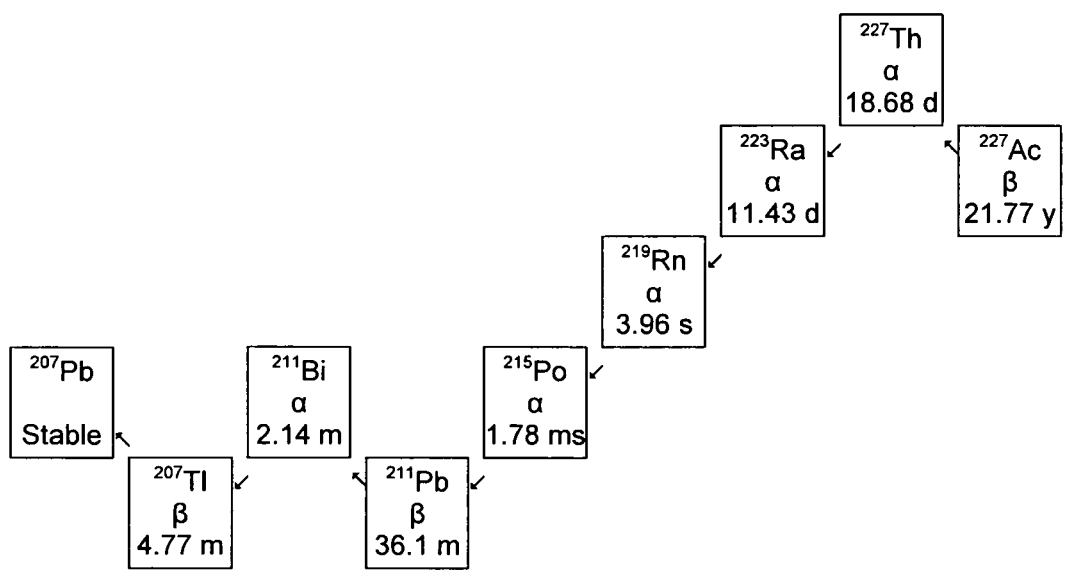
Figure 1. Decay scheme of $^{227}$Ac to stable $^{207}$Pb. Branches with less than 2% probability are omitted.

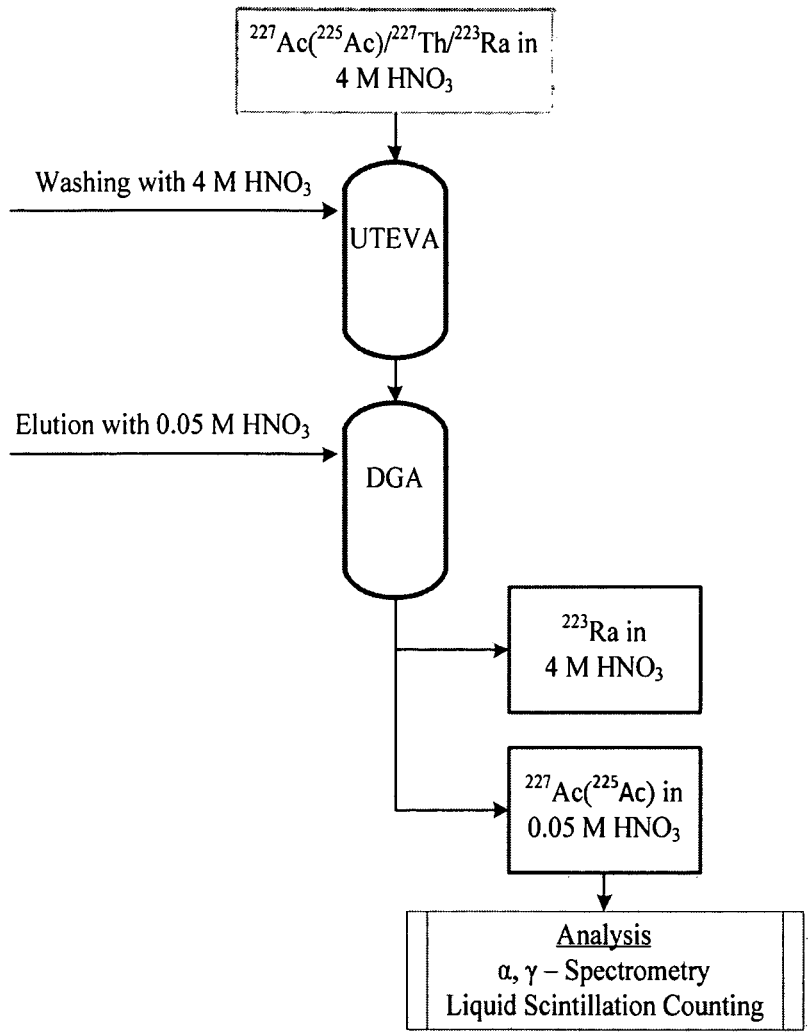
Figure 2. Process flow-chart for actinium, thorium and radium separation and purification using the method of the invention - extraction is shown using aqueous $HNO_3$ of particular concentrations by way of example only.

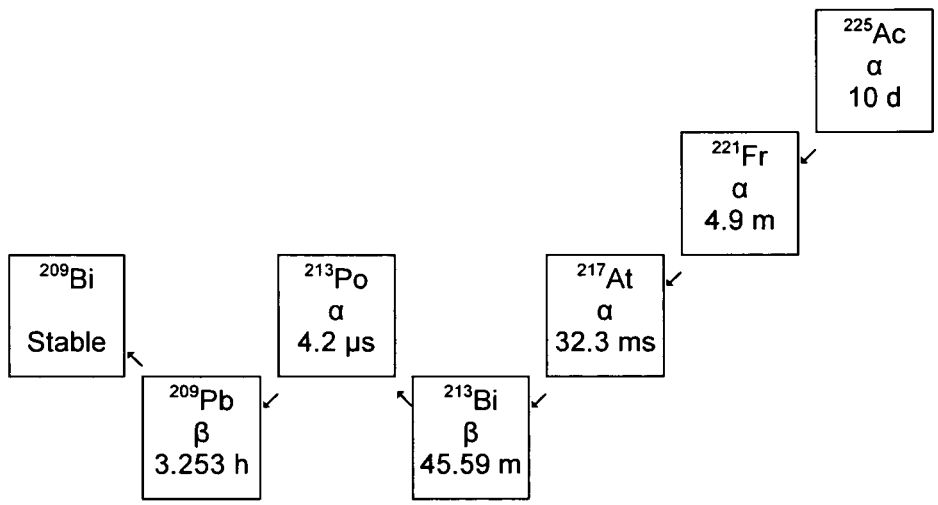
Figure 3. The decay scheme of $^{225}$Ac and daughter radionuclides to stable $^{209}$Bi.
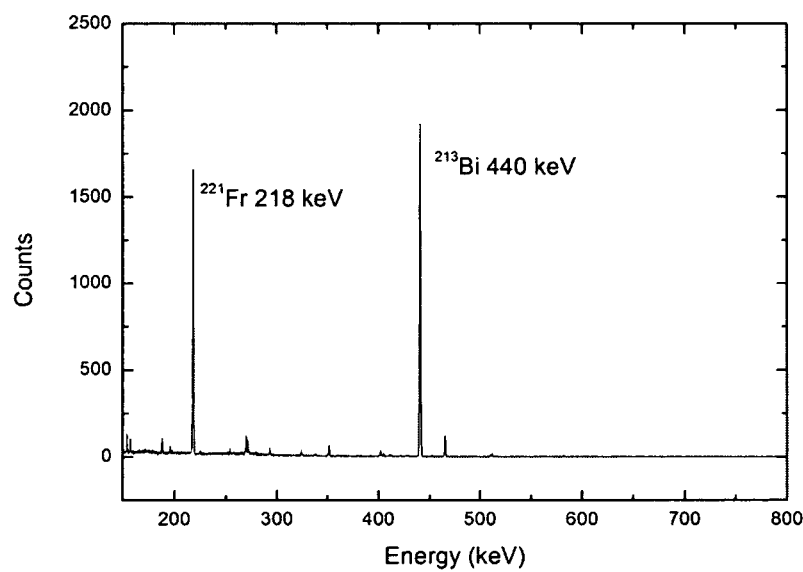
Figure 4. HPGe γ-spectrum of $^{225}$Ac daughters $^{221}$Fr and $^{213}$Bi

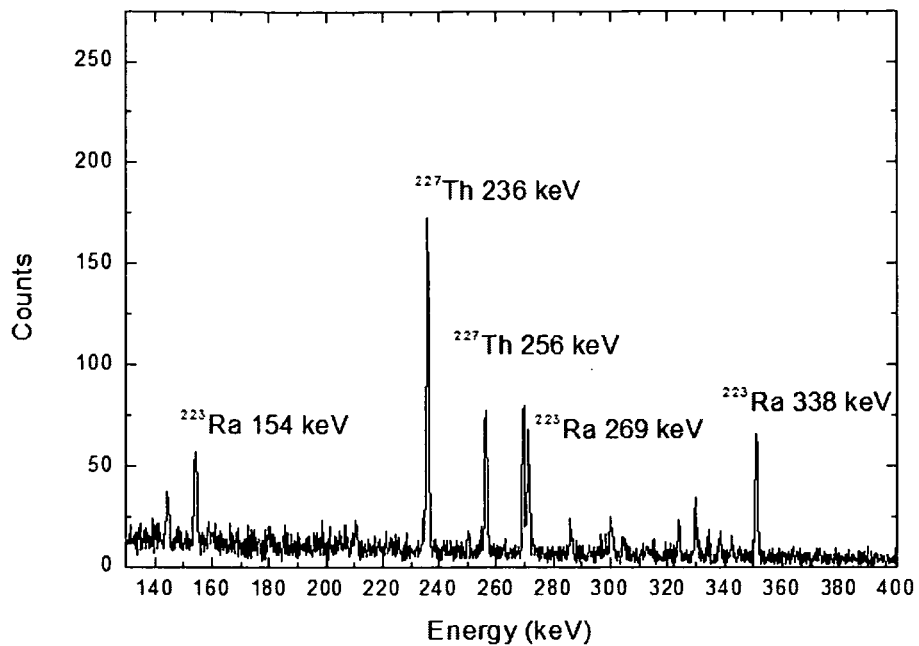
Figure 5. HPGe γ-spectrum of in-growth of $^{227}$Th from $^{227}$Ac 24 hours after separation from $^{223}$Ra-chloride drug substance
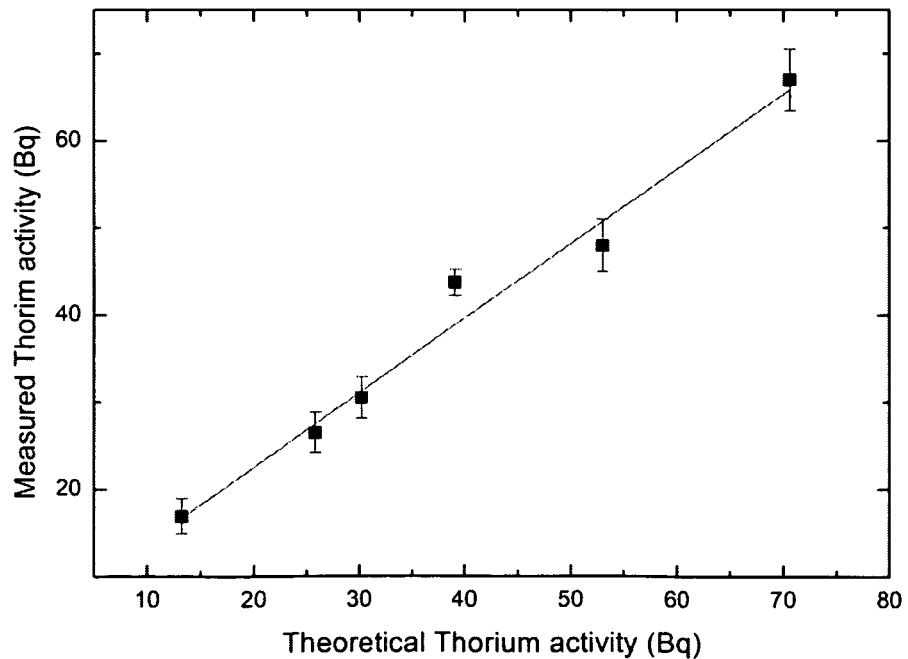
Figure 6. Linearity of measured versus theoretical $^{227}$Th amount in $^{223}$Ra chloride drug substance.

METHOD FOR THE QUANTIFICATION OF 227AC IN 223RA COMPOSITIONS

FIELD OF THE INVENTION

The present invention relates to a novel method for quantifying levels of $^{227}$Ac in $^{223}$Ra compositions, in particular a method which involves solid phase extraction followed by quantification via the in-growth of the $^{227}$Th daughter via γ-spectrometry. The invention further relates to the use of the method of the invention in determining the level of $^{227}$Ac in a $^{223}$Ra composition and to an apparatus for use in the method of the invention.

BACKGROUND

A substantial percentage of cancer patients is effected by skeletal metastases. As many as 85% of patients with advanced lung, prostate and breast carcinoma develop bony metastates (Garret 1993, Nielsen et al, 1991). They are associated with a decline in health and quality of life, ultimately leading to death, often within a few years.

When tumors or metastases cannot be removed by surgery, the conventional approach is to apply external beam radiotherapy and chemotherapy. Both suffer from a lack of selectivity for tumor cells and tumor tissue. As a consequence, treatment most often cannot be applied at curative levels due to toxicity to healthy tissue.

Bone-seeking β-emitters like $^{89}$Sr and $^{153}$Sm complexed with ethylene-diaminetetramethylene-phosphonate (EDTMP) have been used as internal radiotherapy agents in the pain palliation of painful bone metastases especially in prostate cancer. The altered skeletal metabolic activity around many bone metastases results in a local increase in bone formation and uptake of calcium, which is used to construct the hydroxyapatite bone mineral. Bone-seeking radionuclides target this bone adjacent to the tumor deposits. Calcium mimetics, such as strontium $^{89}$Sr, belong to the alkaline earth group of elements in the periodic table. They can be administered as an intravenous radioactive salt that will be incorporated into the newly formed hydroxyapatite in bone metastases. Other radionuclides, such as $^{153}$Sm, require a carrier molecule to achieve selective uptake to the bone, for example, EDTMP. By selectively targeting areas of high metabolic activity in bone, a high therapeutic index is possible.

However, the β-particles are characterized by low-linear energy transfer (LET) typically in the range of 0.2-1.0 keV/μm and a modest relative biological effectiveness (RBE). The use of highly energetic β-particles is restricted by the radiation burden and cell damage to surrounding healthy tissue and especially by the suppression of blood cells in the red bone marrow. Hence, there is an unmet need for more effective bone-targeted treatments that improve quality of life and survival whilst maintaining a favorable safety profile.

The use of α-emitting radionuclides has a major advantage in radiotherapy of cancer. Compared to the low LET values of β-emitters, α-emitters have a mean LET value of 80-100 keV/μm. $^{223}$Ra has shown particular promise. For example, Alpharadin® ($^{223}$RaCl$_2$) has completed a global phase-III clinical trial in patients with castration-resistant prostate cancer (CRPC) and bone metastases. Data shows that Alpharadin prolongs patient overall survival time while offering a well tolerated safety profile (Brady et al, Cancer J., 2013, 19, 71-78). $^{223}$Ra, like $^{89}$Sr, is a calcium mimic and also an alkaline earth element and can be administered as an intravenous radioactive salt. Due to the high LET-values of α-particles and, consequently, their short path-length in human tissue (<100 μm), a highly cytotoxic radiation-dose can be delivered to targeted cancer cells, while damage to the surrounding healthy tissue is limited.

Quality control is an essential part of pharmaceutical manufacture, to ensure the drugs sent to the market are safe and therapeutically active formulations have a performance which is consistent and predictable. The term quality control refers to the sum of all procedures undertaken on each batch to ensure e.g. the identity, activity and purity.

Radionuclidic purity is defined as the percentage of a contaminating radionuclide relative to the wanted radionuclide e.g. $^{227}$Ac relative to $^{223}$Ra with respect to activity in Bq. The primary reason for seeking radionuclidic purity in a radiopharmaceutical is to avoid unwanted administration of radiation to the patient. It is therefore extremely important to strictly control the levels of radionuclidic impurities in radiopharmaceuticals. Radionuclidic impurities may originate from several sources. For example, when a parent-daughter radionuclide generator system is used to produce the radionuclide of interest, the parent nuclides are defined as impurities in the product. Actions must be taken during production to ensure that the parent nuclides are separated from the nuclide of interest and, before release of the finished product for human use, it has to be confirmed that the radioactivity of the radionuclidic impurities are below the limit specified for the product.

Production of $^{223}$Ra for pharmaceutical use is typically based on a radionuclide generator where the mother nuclide $^{227}$Ac ($t_{1/2}$=21.77 years) is adsorbed on a column material. The daughter radionuclides are $^{227}$Th ($t_{1/2}$=18.68 days) and $^{223}$Ra ($t_{1/2}$=11.43 days). $^{223}$Ra is separated by column elution. $^{227}$Ac and its daughter nuclide $^{227}$Th must be strongly retained under conditions were $^{223}$Ra can be eluted. $^{227}$Ac and $^{227}$Th do not have the same bone seeking properties as $^{223}$Ra and are regarded as impurities. Even very low amounts of these nuclides cannot be accepted in the pharmaceutical product. The acceptance criterion for Alpharadin has been set to not more than 0.004% for $^{227}$Ac and not more than 0.5% for $^{227}$Th relative to $^{223}$Ra with respect to activity in Bq. Similar criteria would be expected for other $^{223}$Ra products. Prior to formal release of the product to patients, each produced batch of radiopharmaceutical (e.g. Alpharadin) must be tested to show that it meets the acceptance criteria (adequately defined identity, strength, quality and purity). Due to the inherently short half-life of $^{223}$Ra, the radiopharmaceutical may be released before completion of all tests (e.g. sterility testing). This naturally has the disadvantage that patients could be exposed to a formulation which does not meet all the quality control criteria.

A quantitative determination of $^{227}$Ac is difficult as $^{227}$Ac decays almost entirely by emission of a low-energy β-particle ($E_{\beta,max}$=0.0448 MeV), which is virtually undetectable in the presence of all the energetic α- and β-emitters of the $^{227}$Ac chain (see FIG. 1). $^{227}$Ac also decays by α-emission in 1.38% of its disintegrations. However, direct α-spectrometric determination of $^{227}$Ac is complicated by interferences from the α-emissions of its rapidly growing decay products. Freshly purified $^{227}$Ac emits no analytically useful γ-radiation.

Consequently, many radiometric methods determine $^{227}$Ac indirectly by measurements of the α- and γ-radiations of its daughters, in particular by high-resolution γ-spectrometry of its daughter $^{227}$Th. However, this cannot be determined until 10-12 months after release of the product as analysis must wait until there are sufficiently measurable levels of $^{227}$Th. At this time, the potential amount of $^{227}$Ac contamination is in equilibrium with its daughter $^{227}$Th. Furthermore, the initial amounts of $^{223}$Ra and any $^{227}$Th in the product would have decayed completely. These disadvantages not only lead to inaccuracy of results and increased costs but, more significantly, mean that the result comes too late for the $^{223}$Ra pharmaceutical to be withdrawn from release to patients should it be shown to be contaminated with $^{227}$Ac at levels which would be considered to jeopardise the efficacy of the treatment or the safety of the patient.

In view of the above, there remains a need to develop a new, reliable, accurate and cost-effective radiochemical method for early determination of the potential contamination of $^{227}$Ac in $^{223}$Ra pharmaceuticals, such as Alpharadin (RaCl$_2$). In particular, it would be an advantage to produce a method which is able to give a result in a matter of days rather than months. Ultimately, an analysis method which can be completed prior to release of the product and its administration to patients is attractive. The following criteria set out the desirable features of a new quantification method:

1. $^{227}$Ac should selectively be separated from the precursors.
2. Recovery of $^{227}$Ac>70% and precision>30%
3. Robustness i.e. the analytical result should remain unaffected by small variations in method parameters.
4. Easy to operate in routine production (in terms of time and cost).
5. Sample activity should be as low as possible due to cost and radiation exposure to the operators, and/or
6. Separation and quantification should be fulfilled before release of the product i.e. within 2 days after production of the $^{223}$Ra pharmaceutical (e.g. 223-radium chloride).

The present inventors have surprisingly found that an analytical method employing a tandem column arrangement comprising two different solid phase extraction resins can fulfil some or all of these requirements. In particular, the two columns enable facile separation and isolation of $^{227}$Ac, which can be rapidly quantified.

SUMMARY OF THE INVENTION

Thus, viewed from one aspect, the invention provides a method for the quantification of $^{227}$Ac in a $^{223}$Ra composition, said method comprising:

(i) passing said $^{223}$Ra composition through a first solid phase extraction column A, wherein said column comprises a thorium specific resin (e.g. dipentyl pentylphosphonate UTEVA resin);

(ii) passing the eluate of column A through a second solid phase extraction column B, wherein said column comprises an actinium specific resin (e.g. N, N, N', N'-tetra-n-octyldiglycolamide DGA resin);

(iii) recovering the $^{227}$Ac absorbed onto the resin in column B and determining the amount thereof.

Viewed from another aspect the invention provides a method as hereinbefore described, said method comprising (i) Placing a first solid phase extraction column A comprising a thorium specific resin (e.g. dipentyl pentylphosphonate UTEVA resin) and a second solid phase extraction column B comprising an actinium specific resin (e.g. N, N, N', N'-tetra-n-octyldiglycolamide DGA resin) in series, preferably wherein the output of column A is connected to the input of column B;

(ii) Adding a volume of a $^{223}$Ra composition corresponding to a known activity (e.g. 15 MBq) of $^{223}$Ra to an equal volume of nitric acid, preferably 8 mol/L nitric acid;

(iii) Transferring the sample from step (ii) to the input of the column A;

(iv) Passing said sample through both columns A and B (v) Washing both columns with 20-100 times the combined volume of the two columns (e.g. 5-10 ml) nitric acid, preferably 4 mol/L nitric acid;

(vi) Disconnecting column A from column B;

(vii) Washing column B with 40-200 times its volume (e.g. 5-10 ml) nitric acid, preferably 4 mol/L nitric acid;

(viii) Washing column B with 40-200 times its volume (e.g. 5-10 ml) nitric acid at a concentration less than that used in step (vii), such as 0.05 mol/L nitric acid.

(ix) Determining the amount of $^{227}$Ac present in the eluate from column B obtained in step (viii).

Viewed from another aspect the invention provides the use of a method as hereinbefore described in the quantification of $^{227}$Ac in a $^{223}$Ra composition.

Viewed from another aspect the invention provides apparatus for use in a method as hereinbefore described, wherein said apparatus comprises a first solid phase extraction column A, wherein said column comprises a thorium specific resin (e.g. a dipentyl pentylphosphonate UTEVA resin), and a second solid phase extraction column B, wherein said column comprises an actinium specific resin (e.g. a N, N, N', N'-tetra-n-octyldiglycolamide DGA resin).

DEFINITIONS

The $^{223}$Ra composition of the invention will be understood to be any composition which comprises the radionuclide $^{223}$Ra. The composition will typically be a pharmaceutical composition or a precursor to a pharmaceutical solution and will therefore usually contain the additional components often found in such compositions, e.g. pharmaceutically acceptable diluents, excipients and carriers. Such components are well known in the art. The $^{223}$Ra may be in any form, however the most preferred form is as a salt such as a halide salt, preferably RaCl$_2$ (Alpharadin®), optionally in combination with other Ra salts. It will be appreciated that in order to be compatible with the method of the invention the 223Ra composition must be in solution, typically an aqueous solution, such as an aqueous acid solution.

The method of the invention employs solid phase extraction. This technique is well known in the art, however a brief outline is provided here for completeness.

Solid-Phase Extraction (SPE) has become widely accepted as a substitute for traditional liquid-liquid extraction (LLE) in many types of separation procedures, and especially for those involving low to ultralow concentrations of analyte. SPE is based on the same principles as solvent extraction, which often involves complexation to form a lipophilic compound of the analyte followed by transfer of this compound into an organic phase. In SPE the non-aqueous phase is solid instead of liquid as it is in LLE. SPE is generally faster, more efficient and generates less waste than LLE.

SPE comprises three major components; an inert support, a stationary phase and a mobile phase. The inert support usually consists of porous silica or particles of an organic polymer ranging in size from 50 to 150 μm in diameter. The stationary phase, which is on the surface of the inert support, is selected appropriately depending on the analytes involved. The mobile phase is usually an aqueous acid solution, e.g. nitric or hydrochloric acid.

The method of the invention employs two different stationary phases (resins).

The first resin is a thorium specific resin, typically an UTEVA Resin (Uranium and TEtraValents Actinides), which is mainly used for the separation of uranium and tetravalent actinides. The extractant coated on the inert support is selected to specifically bind thorium in a solution mixture of radium, thorium and actinium. This specificity may be under all conditions, or the conditions used in the methods of the invention may be chosen to ensure specificity.

Extractants suitable for thorium specific resins include phosphonates, particularly alkyl phosphonates. Dialkyl alkyl phosphonates such as those of the following formula (Formula I) are preferred:

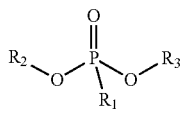
(I)

wherein each of $R_1$-$R_3$ is independently a $C_3$-$C_8$ straight or branched chain alkyl group. Preferably $R_1$-$R_3$ are straight chain alkyl groups. Preferably $R_1$ is a $C_4$-$C_6$ straight chain alkyl group, most preferably n-pentyl. $R_2$ and $R_3$ may be identical or different. Preferably $R_2$ and $R_3$ are identical. Preferably each of $R_2$ and $R_3$ is a straight chain $C_4$-$C_6$ alkyl group, most preferably n-pentyl. A high preferably extractant is dipentyl pentylphosphonate, which has the following structure:

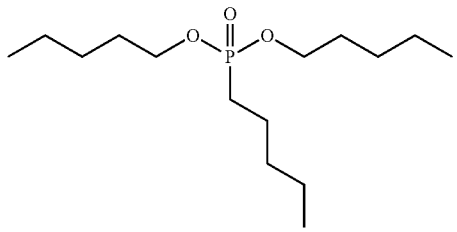 [SMILES: CCCCCOP(=O)(CCCCC)OCCCCC]

The second resin is an actinium specific resin, typically selected to specifically bind actinium in a solution mixture of radium and actinium. This specificity may be under all conditions, or conditions used in the methods of the invention may be selected to ensure specificity.

In some embodiments, the conditions may be such that the actinium specific resin has some degree of affinity for radium as well as actinium and under those conditions both radium and actinium may bind to the second resin. It will be appreciated that, under such circumstances, the method of the invention may require a further step in which the conditions are altered such that any radium which has bound to the second resin may be specifically eluted whilst the actinium remains bound to the resin, before the actinium may be eluted from the second resin.

Preferably, the conditions used in the methods of the invention are chosen such that the second resin does not have any affinity for radium and only actinium binds to the second resin. Thus, in a preferable embodiment, the conditions used in the method of the invention are such that the second resin is specific for actinium. A resin may be considered "specific" for one element over another if that resin will retain at least 90% of the first element under conditions that would elute at least 90% of the second element. This is preferably 95%, more preferably 99%. Typically, the conditions chosen in the methods of the invention are certain concentrations of mineral acids (e.g. nitric acid) in water.

Extractants suitable for actinium specific resins include diglycolamides, particularly tetra-alkyl diglycolamides of the following formula (Formula II):

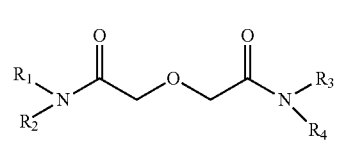
(II)

wherein $R_1$-$R_4$ are independently $C_3$-$C_{12}$ straight or branched chain alkyl groups, preferably $C_5$-$C_{10}$ straight or branched chain alkyl groups. $R_1$-$R_4$ may be identical or different, preferably identical. $R_1$-$R_4$ may all be $C_8$ alkyl groups. A preferred example is N,N,N',N'-tetra-n-octyldiglycolamide (DGA Resin, Normal), which has the following structure:

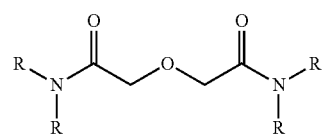

wherein the R-groups are straight chain $C_8$ alkyl groups. The corresponding resin where the R-groups are branched $C_8$ alkyl groups is also of value.

In the context of the invention, the term "eluate" refers to the solution of solvent and dissolved matter resulting from elution, i.e. the mixture of components which elutes following separation using a solid phase extraction column.

The term "eluent" should be understood to be interchangeable with the term "mobile phase". Both terms are well known in the art and are used to refer to the solvent which is passed through a solid phase extraction column and is used to effect separation.

DETAILED DESCRIPTION

The method of the invention comprises the following steps (i) passing a $^{223}$Ra composition (e.g. one containing $^{227}$Ac and $^{227}$Th contaminants) through a first solid phase extraction column A, wherein said column comprises a thorium specific resin (e.g. a dipentyl pentylphosphonate UTEVA resin);

(ii) passing the eluate of column A through a second solid phase extraction column B, wherein said column comprises an actinium specific resin (e.g. a N, N, N', N'-tetra-n-octyldiglycolamide DGA resin);

(ii) recovering the $^{227}$Ac absorbed onto the resin in column B and determining the amount thereof.

In a preferable embodiment, column A and column B are arranged in series such that the eluate from column A passes directly into column B, i.e. wherein the output of column A is connected to the input of column B. The most preferable arrangement is for column A to be positioned above column B such that the eluate from column A drains directly into column B.

The method of the invention relies on the surprising finding that by choice of a resin and column configuration, contaminant $^{227}$Ac can be purified from a mixture of $^{223}$Ra and $^{227}$Th to a sufficient degree to allow for accurate measurement of the $^{227}$Ac via $^{227}$Th in-growth. For example, a UTEVA resin is capable of selectively retaining $^{227}$Th out of a mixture of $^{223}$Ra, $^{227}$Ac and $^{227}$Th and moreover that a DGA resin is capable of selectively retaining $^{227}$Ac from a mixture of $^{227}$Ac and $^{223}$Ra. This results in an efficient separation method. An outline of the process is provided in FIG. 2.

The $^{223}$Ra composition used in the method of the invention comprises $^{223}$Ra. It will typically also comprise both $^{227}$Th and $^{227}$Ac contaminants. Thus, all three radionuclides are usually present in the starting mixture of analytes. As the mixture passes through the first column A, any $^{227}$Th present will absorb onto the thorium specific resin (e.g. UTEVA resin), leaving only $^{223}$Ra and $^{227}$Ac present in the eluate. As this eluate passes though the second column B, any $^{227}$Ac will absorb onto the actinium specific resin (e.g. DGA resin). The $^{223}$Ra will typically remain in the mobile phase. In some embodiments, the actinium specific resin may be washed with additional volumes of mobile phase so as to ensure all $^{223}$Ra is eluted. Thus the total $^{227}$Ac fraction may be obtained and isolated.

Importantly, the $^{227}$Ac fraction, which is bound to the actinium specific resin (e.g. DGA resin), will be substantially free, preferably completely free, of $^{227}$Th and $^{223}$Ra, thereby enabling more facile determination of its quantity via detection of the in-growth of its daughter nuclide, $^{227}$Th at very low levels. In particular, results will not be skewed by levels of $^{227}$Th initially present in the $^{223}$Ra composition or masked by interferences due to other, more energetic, decay chains beginning at $^{227}$Th or $^{223}$Ra. A first isotope may be considered "substantially free" of a second isotope if the second isotope is present at a concentration of less than 1%, preferably less than 0.01%, relative to the concentration of the first isotope. Correspondingly, "completely free" may be considered to correspond to a concentration of less than 0.001% of the second isotope relative to the first isotope.

The mobile phase (eluent) is typically a solution comprising an acid, such as hydrochloric acid or nitric acid. The most preferable acid is nitric acid. Typically, the concentration of any acid used in the method of the invention will be in the range 0.01 to 10 mol/L, preferably 0.02 to 8 mol/L, such as 0.05 to 4 mol/L.

Column A comprises a thorium specific resin, such as a UTEVA resin. The inventors have found that the affinity of an UTEVA resin for $^{227}$Th increases with increasing nitric acid concentration. This is thought to arise because as the concentration of the nitric acid increases so too does the propensity with which the $^{227}$Th will form nitrate complexes. It is believed to be these complexes for which the resin has affinity. Column B comprises an actinium specific resin, such as a DGA resin. DGA resin has been found to have particular affinity for $^{227}$Ac.

The $^{223}$Ra composition used in the methods of the invention typically comprises $^{223}$Ra at a concentration in the range 2 to 30 MBq/ml (e.g. 2.4 to 30 MBq/ml), such as 5 to 20 MBq/ml. The composition will usually be used in the form of an aqueous acid solution, such as nitric acid. The acid will typically have a concentration in the range 4-10 mol/L, for example, 8 mol/L.

In step (iii) the $^{227}$Ac absorbed onto the resin of column B is removed. This may be carried out by a variety of methods but is typically achieved by washing the column with an aqueous acid solution of lower concentration than that which was used as eluent in step (ii), such as 0.05 mol/L nitric acid. The volume of aqueous acid solution used to wash the column may be in the range 16 to 400 times the volume of the column (e.g. 2-20 ml), preferably 40-200 times (e.g. 5-10 ml). The eluate obtained from column B after step (iii) contains $^{227}$Ac. Preferably this eluate is substantially free of $^{227}$Th. For example, the eluate may contain $^{227}$Th at a molar concentration of less than 5%, preferably less than 1% or less than 0.1% and more preferably less than 0.01% relative to the concentration of $^{227}$Ac.

In a highly preferred embodiment, the method of the invention comprises the following steps:
(i) Place a first solid phase extraction column A comprising a thorium specific resin (e.g. a dipentyl pentylphosphonate UTEVA resin) and a second solid phase extraction column B comprising an actinium specific resin (e.g. a N, N, N', N'-tetra-n-octyldiglycolamide DGA resin) in series, preferably wherein the output of column A is connected to the input of column B;
(ii) Add a volume of a $^{223}$Ra composition corresponding to a known activity (e.g. 15 MBq) of $^{223}$Ra to an equal volume of nitric acid, preferably 8 mol/L nitric acid;
(iii) Transfer the sample from step (ii) to the input of the column A;
(iv) Pass said sample through both columns A and B
(v) Wash both columns with 20-100 times the combined volume of the two columns (e.g. 5-10 ml) nitric acid, preferably 4 mol/L nitric acid;
(vi) Disconnect column A from column B;
(vii) Wash column B with 40-200 times its volume (e.g. 5-10 ml) nitric acid, preferably 4 mol/L nitric acid;
(viii) Wash column B with 40-200 times its volume (e.g. 5-10 ml) nitric acid at a concentration less than that used in step (vii), such as 0.05 mol/L nitric acid.
(ix) Determining the amount of $^{227}$Ac present in the eluate from column B obtained in step (viii).

Following isolation of the $^{227}$Ac from the actinium specific resin (e.g. DGA resin), its amount may be quantified by any known method in the art. Typical percentage recoveries of $^{227}$Ac using the method of the invention are in the range 70-100%, such as 72-98%, preferably 74-97% (e.g. 80 to 97% or 80 to 90%). Evidently, for an analytical method reproducibility in recovery of $^{227}$Ac is as important as the absolute recovery. The distribution of such recoveries will thus typically have a standard deviation of no more than 20%, preferably no more than 10%.

Typical methods used to determine the quantity of $^{227}$Ac may involve γ-spectrometry, α-spectrometry and liquid scintillation counting (LSC) with pulse-shape discrimination. The preferred technique is γ-spectrometry, which enables quantification of $^{227}$Ac via in-growth and detection of the daughter $^{227}$Th. Methods for performing γ-spectrometry are well known in the art.

The activity of $^{227}$Ac, which is not directly determinable by γ-ray spectrometry, can be calculated from measurement of the daughter $^{227}$Th. As the specification limit for a $^{223}$Ra pharmaceutical is 0.004% $^{227}$Ac, relative to $^{223}$Ra, an activity of 15 MBq $^{223}$Ra should give an activity of 600 Bq of $^{227}$Ac. The in-growth of $^{227}$Th from $^{227}$Ac is calculated by Equation 1.

$$A_{ingrowth}(^{227}Th) = A_0 \cdot (1 - e^{-\lambda_{Th-227}t}) \quad (1)$$

Due to regulatory requirements for radiopharmaceuticals, the result from radionuclidic purity of a $^{223}$Ra pharmaceutical should be available before release of the product. In order to meet these requirements the maximum in-growth period of $^{227}$Th from $^{227}$Ac should preferably not be more than two days to avoid a prohibitively high loss of $^{223}$Ra by decay before administration. The calculated activity after 24 and 48 hours in-growth of $^{227}$Th from 600 Bq $^{227}$Ac is shown in Table 1.

TABLE 1

Ingrowth of $^{227}$Th from 600 Bq $^{227}$Ac

| Hours after separation | Ingrowth $^{227}$Th (Bq) |
|---|---|
| 24 | 21.9 |
| 48 | 42.9 |

After separation of $^{227}$Ac from $^{227}$Th and $^{223}$Ra, potential traces of $^{227}$Th can be left in the sample (minimum detectable value<1.6 Bq). By counting only one spectrum, the activity of $^{227}$Ac can be overestimated. In the present invention, this issue has been addressed by utilizing two consecutive measurements of the $^{227}$Th daughter: one counted after 24 hours and one after 48 hours from separation. $^{227}$Th activity obtained from analyses after 24 hours is subtracted from $^{227}$Th activity obtained after 48 hours assuming that the in-growth of $^{227}$Th is almost linear in the period. Correction of decay of potential traces of $^{227}$Th ($t_{1/2}$=18.68 days) between 24 and 48 hours after separation, has not been taken into account. It is considered to be sufficiently accurate and within the uncertainty of the measurement.

With the $^{227}$Th activity at measurement time one (24 h) and $^{227}$Th activity at measurement time two (48 h), the unknown, but time independent, activity of the long-lived mother $^{227}$Ac can be calculated by:

$$A_\Delta(^{227}Th) = A_{spectrum2}(^{227}Th) - A_{spectrum1}(^{227}Th) \quad (2)$$

The activity of $^{227}$Ac in the sample at time 0, is based on in-growth of $^{227}$Th. The equations used are given below.

$$A_0(^{227}Ac) = A_\Delta(^{227}Th) \cdot \left(\frac{1}{1 - e^{-\lambda_{Th\text{-}227} t}}\right) \quad (3)$$

where:
$A_0(^{227}Ac)$=the activity of $^{227}$Ac in the $^{223}$Ra pharmaceutical (Bq)
$A_\Delta(^{227}Th)$=the activity of $^{227}$Th produced between measurement time one and measurement time two, e.g. 24 and 48 hours after separation (Bq)
$\lambda_{Th\text{-}227}$=ln 2/18.68 days As seen from Table 1, the activity 24 and 48 hours after in-growth of $^{227}$Th from 600 Bq $^{227}$Ac is 21.9 and 42.9 Bq, respectively. Based on the theoretical calculation of the in-growth of $^{227}$Th and the fact that the separation gives highly purified $^{227}$Ac it was assumed that a counting time of 10000 s in the closest calibrated position (position 5 cm) from the detector surface was sufficient, and satisfactory counting uncertainties were achievable.

Consequently, in the methods of the invention, the quantity of $^{227}$Ac is preferably determined by γ-spectrometry via the in-growth of the daughter nuclide $^{227}$Th, wherein two measurements of the activity of the $^{227}$Th daughter are made. Preferably these measurements are taken at n and 2n hours, wherein n is 12 to 36, preferably at 24 hours and 48 hours, after performing the separation method of the invention. Activity is typically measured over a period of 10000 s at each time point.

In one variant, the method of the invention could be performed in the presence of $^{225}$Ac as a tracer for the chemical yield of $^{227}$Ac to check the accuracy of the results. However, $^{225}$Ac is not commercially available hence it cannot be used in routine analysis at present. Instead, initial verification of the method may be carried out by spiking the $^{223}$Ra composition with $^{225}$Ac, providing quality control data of critical process steps such as correct preparation of acid samples, weighting of correct resins and elution with the correct acid and acid concentration. $^{225}$Ac can be presumed to have the same resin absorption properties as $^{227}$Ac but is easier to detect. $^{225}$Ac may be quantified by the in-growth of the daughter $^{213}$Bi via γ-spectrometry. The decay chain for $^{225}$Ac is shown in FIG. 3.

The method of the invention is suitable for routine analysis of $^{227}$Ac in $^{223}$Ra compositions and can be performed quickly on the same day as preparation of the $^{223}$Ra composition. Preferably separation steps (i) to (iii) can be completed in no more than 2 hours, preferably no more than 1 hour (e.g. 5 minutes to 1 hour). Advantageously, the results from the method of the invention are typically available two days after production i.e. before the product is released and administrated to the patient.

The invention further relates to the use of the methods as hereinbefore described in quantifying levels of $^{227}$Ac in $^{223}$Ra compositions. It should be appreciated that all previous discussion relating to preferable aspects of the invention relate equally to this embodiment.

The invention further relates to apparatus for use in a method as hereinbefore described. The apparatus comprises a first solid phase extraction column A, wherein said column comprises a thorium specific resin (e.g. a dipentyl pentylphosphonate UTEVA resin), and a second solid phase extraction column B, wherein said column comprises an actinium specific resin (e.g. a N, N, N', N'-tetra-n-octyl-diglycolamide DGA resin). Preferably, column A and column B are arranged in series, preferably such that the output of column A is connection to the input of column B. Most preferably, column A is positioned above column B such that the eluate from column A drains directly into column B. It should be appreciated that all previous discussion relating to preferable aspects of the invention relate equally to this embodiment.

FIGURES

FIG. 1—Decay scheme of $^{227}$Ac to stable $^{207}$Pb. Branches with less than 2% probability are omitted.

FIG. 2—Process flow-chart for actinium, thorium and radium separation and purification using the method of the invention—extraction is shown using aqueous HNO$_3$ of particular concentrations by way of example only.

FIG. 3—The decay scheme of $^{225}$Ac and daughter radionuclides to stable $^{209}$Bi.

FIG. 4—HPGe γ-spectrum of $^{225}$Ac daughters $^{221}$Fr and $^{213}$Bi

FIG. 5—HPGe γ-spectrum of in-growth of $^{227}$Th from $^{227}$Ac 24 hours after separation from $^{223}$Ra-chloride drug substance FIG. 6—Linearity of measured versus theoretical $^{227}$Th amount in $^{223}$Ra chloride drug substance

EXAMPLES

The $^{223}$Ra composition utilised in the Examples is RaCl$_2$ (Alpharadin), hereinafter referred to as "Ra-chloride drug substance".

Gamma-spectra were measured with a High-Purity Germanium detector (HPGe) of 50% efficiency (relative to a 3 inch×3 inch NaI detector for a $^{60}$Co source at a distance of 25 cm from the detector surface) coupled to a 8192-channel Multi Channel Analyser (MCA). Spectra were analysed using GammaVision Software (GammaVision-3.2 software, v 6.01, Ortec, Oak Ridge, USA). Calibration of the energy dependent efficiency of the HPGe detector at two fixed positions was performed with a reference source (γ-mixed standard from Eckert & Ziegler) with an overall uncertainty below 4%. The fixed calibration positions were 5 and 20 cm from the detector. The HPGe detector was energy calibrated in an energy range from 59-1400 keV.

In order to evaluate $^{223}$Ra with an activity in the MBq range, an ionization chamber ("dose calibrator", Capintec-CRC15-R) was used. Accurate activity measurements of radionuclides using commercial ionization chambers require that the correct calibration setting ("dial setting") must be applied. For many nuclides, the manufactures of dose calibrators, recommend those calibration settings.

$^{223}$Ra is a relatively novel radionuclide in nuclear medicine and a calibration setting for the radionuclide is therefore not available from commercial manufactures of ionization chambers. A primary standardization of $^{223}$Ra to establish dial settings was performed by the National Institute of Standards and Technology (NIST). The reason is to assure quality-controlled measurements of the radioactivity of $^{223}$Ra during production, quality control and preparation of patient doses.

Measurements with $^{223}$Ra Standard Reference Material (SRM) from NIST were performed in Capintec dose calibrators. The determined calibration setting (dial setting) for the dose calibrator used in the present invention is presented in Table 2.

TABLE 2

$^{223}$Ra dose calibration setting

| Capintec CRC-15R/serial no: | $^{223}$Ra Dose Calibration Setting (dial setting) |
|---|---|
| Serial no 157623, B-lab, Algeta | 262 |

The instruments were qualified, which means verification that the instrument is installed correctly and is capable of operating as intended according to the specifications. Control of the HPGe instrument was performed daily before use by measuring the long-lived radionuclide $^{226}$Ra. The radionuclides $^{57}$Co and $^{137}$Cs are used for daily control of the dose calibrator. The purpose of the quality control of the instruments is to ensure that the instrument provides reliable and consistent results.

Detection of $^{227}$Ac is difficult due to the low energy of its β-radiation and no useful γ-rays. Therefore, in order to easily obtain rapid information concerning the efficiency of the separation of $^{227}$Ac from $^{227}$Th and $^{223}$Ra using the method of the invention the process was carried out using $^{225}$Ac as a radioactive tracer in place of $^{227}$Ac. $^{225}$Ac can be presumed to have the same resin absorption properties as $^{227}$Ac but is easier to detect. Examples 1-3 were carried out with $^{225}$Ac and Examples 4 and 5 with $^{227}$Ac. $^{225}$Ac may be quantified by the in-growth of the daughter $^{213}$Bi via γ-spectrometry.

Uncertainties were calculated as follows:
Uncertainty in the Recovery (Examples 1, 2, 3 and 5)
There is an uncertainty σA in the activity of the "known" (spiked) samples, A.
There is an uncertainty σ$_B$ in the activity of the "found" sample (eluate), B.

$R$ = Recovery (%)

$$R = \frac{B}{A} \cdot 100$$

$$\sigma_R = \sqrt{\frac{\sigma_B^2}{B^2} + \frac{\sigma_A^2 \cdot B^2}{A^4}}.$$

Uncertainty in the Deviation (Example 4)
There is an uncertainty σA in the calculated activity, A.
There is an uncertainty σB in measured activity, B.

$$y = \frac{A - B}{A} \cdot 100$$

$$\sigma'_y = \sqrt{(\sigma_A)^2 + \left(\frac{A}{B^2}\sigma_B\right)^2}$$

Calculation of the Combined Uncertainty (Example 5)
There is an uncertainty σ$_A$ in the activity of the ingrowth of $^{227}$Th after 24 hours, A.
There is an uncertainty σ$_B$ in the activity of the ingrowth of $^{227}$Th after 48 hours, B.
Calculation of the combined uncertainty:

$$f = \sqrt{\sigma_A^2 + \sigma_B^2}$$

EXAMPLE 1

Separation of $^{225}$Ac from $^{227}$Th and $^{223}$Ra using Solid-Phase Extraction Columns Sample Preparation, $^{225}$Ac The $^{225}$Ac used was supplied from the Institute for Transuranium Elements, Karlsruhe, Germany. The solution had a nominal total activity of 6 MBq $^{225}$Ac at the day of receipt and the activity was diluted in 4 mol/L HNO$_3$ to an activity of 3.1 Bq/μL.

A known amount of $^{227}$Th and $^{225}$Ac was added to 15 MBq $^{223}$Ra-chloride drug substance. The activity corresponded to approximately the specification limits of $^{227}$Th and $^{227}$Ac in a $^{223}$Ra-chloride drug substance. The specification states that the activity of $^{227}$Th should be less than 0.5% of $^{223}$Ra activity and the activity of $^{227}$Ac should be less than 0.004% of $^{223}$Ra. Table 3 gives the activities of $^{225}$Ac and $^{227}$Th used in the experiments.

TABLE 3

Activities (Bq) of $^{227}$Th and $^{225}$Ac in experiment I and II.

| Nuclide | Experiment I | Experiment II |
|---|---|---|
| $^{227}$Th (kBq) | 66.9 ± 2.2[1] | 74.6 ± 2.4[1] |
| $^{225}$Ac (Bq) | 497.7 ± 23.9[1] | 667.8 ± 33.4[1] |

[1])Uncertainty in the activity (2 σ)

Activities were determined using the following methods:
$^{223}$Ra-chloride drug substance was transferred to two 20 mL vials (each with an activity of 15 MBq) and measured in a dose calibrator in dial setting 262. The γ-rays of $^{225}$Ac and $^{227}$Th solutions were measured with an HPGe detector in the calibrated position 5 cm and 20 cm, respectively.

For determining the areas of the γ-peaks in the energy spectrum, ORTEC GammaVision software was used. The energy and photon yield data are taken from Evaluated Nuclear Data File (ENSDF—available from http://www.nndc.bnl.gov/nudat2/—21 Jun. 2013). The most abundant γ-lines, given in Table 4, are used for the activity calculation.

TABLE 4

γ-ray energies and emission probabilities (percent) used for the determination of radionuclide activities.
Library: Ra_223_DS_Ac_225_ENSDF_20_sep_2012.Lib

| Nuclide | Energy | Percent | Half-Life |
|---|---|---|---|
| Ac-225 | 99.80 | 1.0000 | 10 Days |
| Th-229 | 124.55 | 0.6900 | 7932 Yrs. |
| Th-229 | 136.99 | 1.1800 | 7932 Yrs. |
| Ra-223 | 144.24 | 3.2700 | 11.43 Days |
| Ra-223 | 154.21 | 5.7000 | 11.43 Days |
| Th-229 | 156.00 | 1.1900 | 7932 Yrs. |
| Th-229 | 204.70 | 0.6000 | 7932 Yrs. |
| Th-229 | 210.85 | 2.8000 | 7932 Yrs. |
| Fr-221 | 218.12 | 11.4000 | 4.9 Min. |
| Th-227 | 235.96 | 12.9000 | 18.68 Days |
| Ra-223 | 269.46 | 13.9000 | 11.43 Days |
| Ra-223 | 323.87 | 3.9900 | 11.43 Days |
| Th-227 | 286.09 | 2.4000 | 18.68 Days |
| Ra-223 | 338.28 | 2.8400 | 11.43 Days |
| Bi-211 | 351.06 | 12.9200 | 11.43 Days |
| Rn-219 | 401.81 | 6.6000 | 11.43 Days |
| Pb-211 | 427.09 | 1.7600 | 11.43 Days |
| Bi-213 | 440.45 | 25.9400 | 45.59 Min. |
| Ra-223 | 445.03 | 1.2900 | 11.43 Days |
| Th-229 | 454.00 | 0.0100 | 7932 Yrs. |
| Pb-211 | 704.64 | 0.4620 | 11.43 Days |
| Pb-211 | 832.01 | 3.5200 | 11.43 Days |

Data was taken from ENSDF.

Production of $^{225}$Ac is based on a $^{229}$Th generator from which $^{225}$Ac is eluted. The γ-lines from $^{229}$Th used for activity calculation are seen in Table 4. No traces of $^{229}$Th were found in the sample.

Preparation and Conditioning Procedure of the UTEVA and DGA Columns

The extraction-chromatographic resins as well as the prefilter material were packed in 2 ml disposable polystyrene plastic gravity-feed columns (obtained from Fisher Scientific). The following steps were carried out:
  Weigh in approximately 100 mg of UTEVA resin and 50 mg of DGA resin.
  Transfer the resin to two 20 ml plastic vials and add approximately 3 ml of 4 mol/L $HNO_3$ to each. Swirl to mix.
  Prior to packing of the two columns, transfer a filter to the columns. Push the filter down to the base of the columns.
  Transfer the solution into the reservoir. Place a filter on the top of the UTEVA resin and DGA resin.
  Push the filter and the resin down.
  Discard the acid above the top filter. Add 2-3 ml of 4 mol/L $HNO_3$. Discard the acid again.
  Remove the bottom plug from the columns.
  Add 2-3 ml 4 mol/L $HNO_3$. Allow to drain.

Two-Column Separation Procedure
  Place one UTEVA resin column and one DGA resin column in the column rack in series, i.e., solutions from the UTEVA resin column (on top) will drain into the DGA resin column (on bottom) (see FIG. 1).
  Based on $^{223}$Ra-chloride drug substance radioactivity concentration, MBq/ml, pipette accurately a volume corresponding to 15 MBq into a 20 ml vial. Add an equal amount of 8 mol/L $HNO_3$.
  Known activities of $^{227}$Th and $^{225}$Ac were added to the $^{223}$Ra-chloride solution, according to Table 3.
  Use a plastic pipette to transfer the sample to the top of the UTEVA column. $^{225}$Ac and $^{223}$Ra will elute from the UTEVA column into the DGA column while $^{227}$Th will absorb to the UTEVA column.
  Wash the columns with 5 ml of 4 mol/L $HNO_3$.
  Disconnect the UTEVA column from the DGA column.
  Transfer 5 ml of 4 mol/L $HNO_3$ onto the top of the DGA column. $^{223}$Ra will elute from the column while $^{227}$Ac will stay trapped on the DGA column.
  Elute the DGA column with 5 ml 0.05 mol/L $HNO_3$. This will remove $^{227}$Ac from the column.

It will be appreciated that in routine analysis (separation of $^{227}$Ac, $^{227}$Th and $^{223}$Ra) no addition of $^{227}$Th and $^{225}$Ac to the $^{223}$Ra-chloride solution was carried out, the solution was transferred directly to the UTEVA column.

Two separation experiments with $^{225}$Ac were conducted. After complete separation, the columns and eluates were counted the day after separation with an HPGe detector. $^{225}$Ac has no suitable γ-rays and therefore it is quantified through its daughter $^{213}$Bi. $^{225}$Ac is in secular equilibrium with is daughters after 24 hours. $^{225}$Ac was identified through the measurement of the daughters $^{221}$Fr and $^{213}$Bi. A spectrum of the highly purified $^{225}$Ac eluate is shown in FIG. 4. The γ-ray energies and intensities, used for the identification and quantification of $^{225}$Ac and $^{227}$Th, are presented in Table 4.

Percentage recovery for $^{225}$Ac obtained from experiments I and II was 97% and 86% respectively. Results are reported in Table 5. These results show that the extraction resins UTEVA and DGA give an effective, reproducible, robust and rapid separation of $^{225}$Ac from $^{227}$Th and $^{223}$Ra. The DGA resin shows a strong retention of $^{225}$Ac in nitric acid and efficient stripping of $^{225}$Ac in dilute nitric acid. As seen from Table 5, the breakthrough ("recovery" in Table 5) of $^{227}$Th and $^{223}$Ra in the final eluate was less than $2·10^3$ and $8·10^4$, respectively. Moreover, only traces of the initial amounts of $^{223}$Ra and $^{227}$Th were detected in the eluates. This shows that the separation procedure of $^{225}$Ac from $^{227}$Th and $^{223}$Ra with UTEVA and DGA column is highly effective. Thus, the method demonstrates that separation of $^{227}$Ac, $^{227}$Th and $^{223}$Ra will also be effective.

TABLE 5

Activity (Bq) of $^{225}$Ac, $^{22}$Th and $^{227}$Ra on the UTEVA and DGA column after separation and in the eluate obtained by γ-ray spectrometry. Uncertainty in the activity (2 σ). Activities added at the start of the experiment are seen in Table 3.

| | Experiment I | | | Experiment II | | |
|---|---|---|---|---|---|---|
| | $^{225}$Ac (Bq) | $^{227}$Th (kBq) | $^{223}$Ra (Bq) | $^{225}$Ac (Bq) | $^{227}$Th (kBq) | $^{223}$Ra (Bq) |
| UTEVA | N.D. | 68.4 ± 2 | N.D. | <11.6[1] | 68.4 ± 2 | N.D. |
| DGA | 23.3 ± 3 | N.D. | 20.5 ± 1 | 63.5 ± 1 | N.D. | <12.9[1] |

TABLE 5-continued

Activity (Bq) of $^{225}$Ac, $^{22}$Th and $^{227}$Ra on the UTEVA and DGA column after separation
and in the eluate obtained by γ-ray spectrometry. Uncertainty in the activity
(2 σ). Activities added at the start of the experiment are seen in Table 3.

| | Experiment I | | | Experiment II | | |
|---|---|---|---|---|---|---|
| | $^{225}$Ac (Bq) | $^{227}Th$ (kBq) | $^{223}$Ra (Bq) | $^{225}$Ac (Bq) | $^{227}Th$ (kBq) | $^{223}$Ra (Bq) |
| Eluate[2] | 483.6 ± 20 | <0.2[1] | 41.5 ± 4 | 74.7 ± 6 | N.D. | 84.4 ± 16 |
| | | | | 423.0 ± 20 | <1.6[1] | 21.6 ± 1 |
| | | | | 73.1 ± 5 | <0.3[1] | 8.4 ± 1 |
| Recovery (%) | 97 ± 6 | 3 · 10$^{-4}$ | 2.8 · 10$^{-4}$ | 86 ± 6 | 2.1 · 10$^{-3}$ | 7.6 · 10$^{-4}$ |

[1] minimum detectable amount (MDA)
[2] In Experiment II, three fractions of 1.7 ml of the eluate were collected and counted

EXAMPLE 2

Testing of the Robustness of the Method

Robustness of the method was tested by using new batches (new lot number) of UTEVA and DGA resin. The robustness of an analytical procedure is a measure of its capacity to remain unaffected by small variations in method parameters and provides an indication of its reliability during normal usage.

A total of three experiments (I, II and III) were conducted with 15 MBq $^{223}$Ra-chloride drug substance spiked with known activity of $^{225}$Ac. The activity of $^{225}$Ac is shown in Table 6. In addition, approximately 75 kBq of $^{227}$Th was added. The separation was performed according to the procedure given in Example 1.

Percentage recovery of $^{225}$Ac obtained after eluting with 5 ml 0.05 mol/L HNO$_3$ was 68, 81 and 77%. The recoveries obtained were lower than for the UTEVA and DGA batches used in Example 1. It was therefore decided to increase the eluting volume (in addition to the 5 ml already added) by adding 2 times a volume of 2.5 ml of 0.05 mol/L HNO$_3$. The results are presented in Table 6. The percent recovery of $^{225}$Ac increased to 81, 85 and 84% and this is comparable to the previously obtained result. This shows that the method is robust with regards to new batches (new lot) of resins. However, the eluting volume may require adjustment to obtain sufficient recoveries (>70%).

TABLE 6

Measured $^{225}$Ac activity (Bq). Testing of robustness of
the method by using new batch of UTEVA and DGA resins.

| | Experiment I | Experiment II | Experiment III |
|---|---|---|---|
| $^{225}$Ac spike | 652.4 ± 47 | 609.4 ± 52 | 712.6 ± 50 |
| Eluate (5 ml) | 442.7 ± 35 | 491.2 ± 39 | 547.2 ± 43 |
| Eluate (2.5 ml) | 56.4 ± 1 | 23.7 ± 4 | 37.5 ± 1 |
| Eluate (2.5 ml) | 27.5 ± 8 | <1.9 | 11.7 ± 6 |
| Recovery (%) | 81 ± 9 | 85 ± 10 | 84 ± 9 |

Uncertainty in the activity (2 σ).

EXAMPLE 3

Testing of the Range of the Method

Analytical methods developed by a pharmaceutical company must be validated. The method should be validated in the range from reporting limit to at least 120% of the specification limit. In the previous experiments, the amount of $^{225}$Ac has been added related to the specification limit. As the specification limit is 0.004% relative to $^{223}$Ra, approximately 600 Bq of $^{225}$Ac has been added to 15 MBq $^{223}$Ra. The purpose of Example 3 was to add lower and higher activities of $^{225}$Ac. The reason was to cover the range of amounts of $^{227}$Ac which would be used during validation. Three experiments were conducted with various amounts of $^{225}$Ac.

Results

Percent recovery of $^{225}$Ac obtained after elution of 10 ml 0.05 mol/L HNO$_3$ were 91, 74 and 92%. The results are presented in Table 7. This shows that the recovery is acceptable (>70%) from 46 to 172% of the specification limit.

TABLE 7

Measured $^{225}$Ac activity (Bq). Three experiments with an $^{225}$Ac
activity ranging from 46-172% of the specification limit of $^{227}$Ac.

| | Experiment I | Experiment II | Experiment III |
|---|---|---|---|
| $^{225}$Ac Spike | 1033.3 ± 64 | 644.1 ± 32 | 278.3 ± 15 |
| Eluate (5 ml) | 872.8 ± 58 | 459.9 ± 38 | 241.0 ± 26 |
| Eluate (5 ml) | 70.5 ± 14 | 15.7 ± 6 | 15.7 ± 6 |
| Recovery (%) | 91 ± 8 | 74 ± 7 | 92 ± 12 |

The uncertainties are given as 2 σ.

EXAMPLE 4

Determination of Counting Conditions

Separation of $^{227}$Ac, $^{227}$Th and $^{223}$Ra was performed by UTEVA and DGA columns as described in Example 1, with the difference that a sample of 534±21 Bq (2σ) $^{227}$Ac was added to the column rather than the $^{225}$Ac spike and supplemental $^{227}$Th. Prior to separation, the sample was counted with a HPGe detector and quantified via its daughter $^{227}$Th as $^{227}$Ac was in equilibrium with its daughters for this sample.

Results $^{227}$Ac was eluted from the DGA column with 0.05 mol/L HNO$_3$ and counted in the calibrated position 5 cm from the detector surface for 10000 s after approximately 1 and 2 days. Results are given in Table 8.

TABLE 8

Results from γ-ray spectrometry ingrowth of $^{227}$Th from $^{227}$Ac.

| Days | Activity Calculated (Bq) | Measured activity (Bq) | Deviation from Calculated (%) |
|---|---|---|---|
| 1.08 | 21.0 ± 0.8 | 21.3 ± 1.2 | −1.4 ± 0.8 |
| 2.08 | 39.7 ± 1.5 | 39.2 ± 2.8 | 1.3 ± 1.5 |

The uncertainties are given as 2 σ.

As seen from Tabl, satisfactory counting uncertainties (<7%, 2σ) were achievable for a sample counted for 10000 s in position 5 cm from the detector. There was no difference between calculated and measured activity.

EXAMPLE 5

Validation of the Method

Analytical methods developed by a pharmaceutical company must be validated. Analytical method validation is the process to confirm that the analytical procedure employed for a specific test is suitable for its intended use, i.e. to ensure reliability, consistency and accuracy of the analytical data. In order to demonstrate the applicability of the methods of the invention to commercial applications it was validated according to ICH Harmonized Guideline. Prior to a formal method validation it is mandatory to set up a protocol with test parameters to be evaluated and appropriate acceptance criteria.

The method was validated in terms of selectivity, accuracy, precision (repeatability/intermediate precision), linearity, range, limit of detection (LOD) and limit of quantification (LOQ). Robustness of the method was performed in Example 2 in terms of different lots of resins and was hence was not repeated in this Example.

The ICH guideline says nothing about acceptance criteria for the different parameters. However, accuracy in terms of recovery between 80-120% and a precision of ±20% is normally regarded as acceptable. This is applicable for impurities >0.1% of the active ingredient. As the specification for the impurity $^{227}$Ac in $^{223}$Ra-chloride drug substance is set as low as 0.004% relative to $^{223}$Ra, a broader acceptance was required.

Samples of $^{223}$Ra-chloride drug substance were spiked with known amounts of $^{227}$Ac and $^{227}$Th. Validation parameters and corresponding acceptance criteria for the method validation are given in Table 9.

TABLE 9

Validation parameters and acceptance criteria

| Validation Parameter | | Acceptance Criteria |
|---|---|---|
| Selectivity | | The energies of the γ-rays of $^{227}$Th are clearly resolved from the energies of the radionuclides potentially present in the matrix. |
| Accuracy of $^{227}$Ac as % recovery | | 70-130% |
| Repeatability (% RSD) | 60% of specification (n = 3) | <30% |
| | 100% of specification (n = 3) | <30% |
| | 140% of specification (n = 3) | <30% |
| Linearity, Correlation coefficient, r | | >0.95 |
| LOQ (Bq) | | NA[1] |
| LOD (Bq) | | NA[1] |

[1]NA = Not applicable

Experimental Parameters

According to ICH, accuracy and repeatability should be assessed using a minimum of 9 determinations over a minimum of 3 concentration levels covering the specified range (e.g. 3 concentrations/3 replicates). The recommended range for validation of an impurity method is from reporting limit to at least 120% of the specification. Samples from 60-140% of the specification limit were prepared according to Table 10.

TABLE 10

Overview of samples used in method validation.
$^{223}$Ra is spiked with $^{227}$Ac and $^{227}$Th. The $^{227}$Ac activity is from 60-140% of the specification limit.

| % of specification | $^{227}$Ac Activity (Bq) | $^{227}$Th Activity (kBq) | $^{223}$Ra Activity (MBq) | Replicates |
|---|---|---|---|---|
| 60 | 360 | 75 | 15 | 3 |
| 80 | 480 | 75 | 15 | 1 |
| 100 | 600 | 75 | 15 | 3 |
| 120 | 720 | 75 | 15 | 1 |
| 140 | 840 | 75 | 15 | 3 |

The method stipulates a sample size of 15 MBq. According to specifications, the amount of $^{227}$Ac and the amount of $^{227}$Th should be less than 0.004% and less than 0.5% relative to $^{223}$Ra activity, respectively. As the decided validation range was from 60 to 140% of the specification, spikes of $^{227}$Ac from 360 to 840 Bq were prepared. The content of $^{227}$Th was held constant i.e. 75 kBq (0.5% of the specification). The $^{227}$Ac and $^{227}$Th stock solutions were both made in 4 mol/L HNO$_3$ and the activities were approximately 5 Bq/μL and 0.5 kBq/μL, respectively. To determine the exact activity of $^{227}$Ac spike solutions, counting with a HPGe detector in position 5 cm for 1000 s was performed. The counting time was selected to give a counting uncertainty (1 σ) of less than approximately 3%, which was regarded as adequate. Counting of $^{227}$Th stock solutions was performed in position 20 cm for 300 seconds.

$^{223}$Ra from three $^{223}$Ra-chloride drug substance batches were pooled. Contamination of $^{227}$Ac in the pooled batch was determined. An aliquot of 15 MBq was taken from the pooled sample and analyzed according to the method described in Example 1. This was done to ascertain if any correction needed to be made to the above results on account of background contamination of the samples with $^{227}$Ac. No traces of $^{227}$Ac in the pooled $^{223}$Ra-chloride drug substance were found. Hence, no correction was performed.

Results—Selectivity

Selectivity is the ability of the measurement to assess the analyte without any interference from other components in the matrix. At the time of analysis, radionuclides present in $^{223}$Ra-chloride drug substance have been separated from $^{227}$Ac according to the method presented in Example 1. β-decay of $^{227}$Ac does not produce emissions of γ-rays that are appropriate for γ-detection. Traces of $^{223}$Ra and its daughters can remain in the sample after purification and the selectivity of the method is demonstrated by comparing the energies of the γ-rays of $^{227}$Th with the energies of $^{223}$Ra and its γ-emitting daughters, $^{219}$Rn, $^{211}$Pb and $^{211}$Bi, and by showing that they are clearly separated and identifiable. The γ-ray used for quantification of $^{227}$Th is 236.0 keV, which is the most abundant γ-line of $^{227}$Th (12.9%).

The γ-ray energies characteristic of $^{227}$Th, $^{223}$Ra and daughters are shown in Table 11. A spectrum acquired 24 hours after separation of $^{227}$Ac from $^{223}$Ra-chloride drug substance is shown in FIG. 5.

TABLE 11

γ-ray energies of $^{223}$Ra and its daughters and $^{227}$Th

| $^{223}$Ra | $^{219}$Rn | $^{211}$Pb | $^{211}$Bi | $^{227}$Th |
|---|---|---|---|---|
| 144.2 | | | | |
| 154.2 | | | | |
| | | | | 210.6 |
| | | | | 236.0 |
| | | | | 256.2 |
| 269.5 | | | | |
| | 271.2 | | | |
| | | | | 286.1 |
| | | | | 300.0 |
| | | | | 304.5 |
| 323.9 | | | | |
| | | | | 329.9 |
| 338.3 | | | | |
| | | | 351.1 | |
| | 401.8 | | | |
| | | 404.9 | | |
| | | 427.1 | | |
| | | 704.6 | | |
| | | 832.0 | | |

(Data taken from Evaluated Nuclear Structure Data File (ENSDF) database)

As seen from FIG. 5, the γ-ray used for quantification of $^{227}$Th is distinctly and visibly separated from the energies of other nuclides. There are no interferences from the matrix. The method is considered specific and the acceptance requirement was fulfilled.

Results—Accuracy

The accuracy of the method was determined by performing recovery experiments on $^{223}$Ra-chloride drug substance spiked with five levels of $^{227}$Ac at 60%, 80%, 100%, 120%, and 140% of the specification limit of $^{227}$Ac. The solutions were additionally spiked with $^{227}$Th amounts corresponding to the $^{227}$Th specification limit. For the 60%, 100% and 140% levels the solutions were prepared in three-fold. For the 80% and 120% level the solutions were prepared once.

Solutions were analyzed as described in Example 1. Each solution was measured twice. First measurement was performed 24±1 hour after sample preparation, the second measurement was performed 48±1 hour after sample preparation.

Accuracy as the percent recovery was determined using the measured $^{227}$Ac content calculated as described in Equation 4.

$$\text{Recovery} = \frac{\text{Measured content}}{\text{Nominal content}} \times 100 \qquad (4)$$

Results are presented in Table 12.

TABLE 12

Results for the accuracy (as recovery) of the method. Samples in the range of 60-140% of the specification limit for $^{227}$Ac relative to $^{223}$Ra.

| Level [%] | Nominal activity $^{227}$Ac [Bq][1] | $^{227}$Th after 24 hours [Bq][1] | $^{227}$Th after 48 hours [Bq][1] | Calculated activity $^{227}$Ac [Bq][2] | Diff between measurement 1 and 2 [Days] | Recovery [%][2] |
|---|---|---|---|---|---|---|
| 60 | 323 ± 22.0 | 20.4 ± 2.7 | 31.6 ± 3.0 | 303 ± 4.0 | 1.0 | 94.0 ± 6.5 |
|  | 322 ± 22.5 | 10.9 ± 2.6 | 25.7 ± 2.9 | 397 ± 3.9 | 1.0 | 123.2 ± 8.7 |
|  | 359 ± 23.0 | 16.9 ± 2.0 | 26.5 ± 2.3 | 263 ± 3.0 | 1.0 | 73.3 ± 4.8 |
| 80 | 460 ± 27.6 | 16.9 ± 2.5 | 30.5 ± 2.9 | 369 ± 3.8 | 1.01 | 80.3 ± 4.9 |
| 100 | 540 ± 30.2 | 22.1 ± 2.0 | 42.7 ± 2.8 | 578 ± 3.4 | 0.98 | 107.0 ± 6.0 |
|  | 591 ± 31.9 | 24.0 ± 2.1 | 43.8 ± 2.9 | 556 ± 3.6 | 0.97 | 94.1 ± 5.1 |
|  | 527 ± 29.5 | 21.1 ± 3.2 | 40.1 ± 4.1 | 535 ± 5.2 | 0.97 | 101.5 ± 5.8 |
| 120 | 715 ± 35.8 | 26.7 ± 2.3 | 53.8 ± 2.9 | 655 ± 3.7 | 1.14 | 91.6 ± 4.6 |
| 140 | 868 ± 39.9 | 36.0 ± 4.9 | 62.8 ± 5.1 | 735 ± 7.1 | 1.00 | 84.7 ± 4.0 |
|  | 861 ± 41.3 | 31.0 ± 3.2 | 56.7 ± 3.6 | 706 ± 4.8 | 1.00 | 82.0 ± 4.0 |
|  | 803 ± 38.5 | 36.8 ± 4.6 | 61.0 ± 4.5 | 662 ± 6.4 | 1.00 | 82.4 ± 4.0 |
| Mean recovery [%] (n = 11) |  |  |  |  |  | 92.2 |
| Relative standard deviation of the recovery [%] (n = 11) |  |  |  |  |  | 15.5 |
| Confidence interval (95%) of recovery [%] |  |  |  |  |  | 82.2-102.1 |

[1]Uncertainty in the activity (2 σ).
[2]Combined and recovery uncertainty

As seen from Table 12, the single percent recovery and the mean (n=11) is all within the criteria of acceptance (70 to 130%, see Table 9). The method is considered sufficiently accurate for the determination of $^{227}$Ac content in the range from 60% to 140% of the specification limit which corresponds to 0.002%-0.006% of $^{227}$Ac in $^{223}$Ra-chloride drug substance at release. The requirement is thereby fulfilled.

The uncertainties in recovery were in the range from 4-8.7%, comparable to 2σ in the counting statistics, and it was the lowest activity which gave rise to the largest uncertainties. A contribution to the uncertainties is the uncertainty in the spiked value. This is not relevant for analyses of "normal" $^{223}$Ra-chloride drug substance samples and hence the real uncertainties are lower.

Results—Precision

The repeatability of the method was determined by calculating the relative standard deviation (RSD) for three replicates of $^{227}$Ac in $^{223}$Ra-chloride drug substance at three different levels at 60% (corresponding to 0.002% of $^{227}$Ac), 100% (0.004% of $^{227}$Ac), and 140% (0.006% of $^{227}$Ac) of the specification limit. For each level, the solutions were prepared in triplicate and analyzed as described in Example 1. Results are presented in Table 13.

As seen from Table 13, the mean relative standard deviations were ≤30% for all three levels. The method is considered sufficiently precise and the acceptance requirement was fulfilled (see Table 9).

TABLE 13

Results for the precision of the method

| Level [%] | Recovery $^{227}$Ac [%] | Mean (n = 3) [%] | RSD (n = 3) [%] |
|---|---|---|---|
| 60 | 94.0 | 96.8 | 25.9 |
|  | 123.2 |  |  |
|  | 73.3 |  |  |
| 100 | 107.0 | 100.9 | 6.4 |
|  | 94.1 |  |  |
|  | 101.5 |  |  |
| 140 | 84.7 | 83.0 | 1.7 |
|  | 82.0 |  |  |
|  | 82.4 |  |  |

Results—Intermediate Precision

Intermediate precision expresses within-laboratory variations in terms of e.g. different days, different analysts and different equipment. The intermediate precision was in this case determined in terms of different days. Separation was performed on four different days and the results are given in Table 14.

TABLE 14

Intermediate precision.

| Level [Days] | Measured activity Ac-227 [Bq] |
|---|---|
| 1 | 94.0 |
| 1 | 123.2 |
| 2 | 73.3 |
| 3 | 107.0 |
| 3 | 94.1 |
| 3 | 101.5 |
| 4 | 84.7 |
| 4 | 82.0 |
| 4 | 82.4 |
| Mean recovery [%] (n = 9) | 93.6 |
| RSD [%] (n = 9) | 16.3 |

As seen from Table 14, the mean relative standard deviation was ≤30% for all four days. Data show that the results from different days are comparable and that the acceptance requirement are thereby fulfilled.

Results—Linearity

Linearity is the ability to generate a response which is directly proportional to the concentration of an analyte in a sample. To demonstrate the linearity of the method, a sample with an activity of 359±23 Bq $^{227}$Ac was used. The sample was separated according to the procedure described in Example 1. The in-growth of $^{227}$Th from $^{227}$Ac was measured 6 times in a period from 1 to 6 days after separation. The corresponding theoretical activity was calculated using Equation 1. Results are presented in Table 15 and the plot of signals is displayed in FIG. 6.

TABLE 15

Results for the linearity of the method

| Time from separation [Days] | Theoretical $^{227}$Th [Bq] | Measured activity $^{227}$Th [Bq] |
|---|---|---|
| 1.0 | 13.2 ± 0.8 | 16.9 ± 2.0 |
| 2.0 | 25.8 ± 1.6 | 26.5 ± 2.3 |
| 2.4 | 30.2 ± 2.0 | 30.5 ± 2.4 |
| 3.1 | 39.1 ± 2.5 | 43.7 ± 1.5 |

TABLE 15-continued

Results for the linearity of the method

| Time from separation [Days] | Theoretical $^{227}$Th [Bq] | Measured activity $^{227}$Th [Bq] |
|---|---|---|
| 4.3 | 53.0 ± 3.4 | 48.0 ± 3.0 |
| 5.9 | 70.6 ± 4.5 | 67.0 ± 3.5 |
| Regression line |  |  |
| Slope |  | 0.8629 |
| Intercept [Bq] |  | 5.4606 |
| Correlation coefficient (r) |  | 0.9797 |

The linearity curve was measured with $^{227}$Th activities ranging from 17-67 Bq. This range covers the $^{227}$Th activities which are measured from decay of $^{227}$Ac in specification levels of 78-156% (100% gives an activity of 21.9 Bq after 24 hours and 42.9 Bq after 48 hours, see Table 1). The measured $^{227}$Th activity is plotted as a function of the theoretical $^{227}$Th activity. The correlation coefficient was determined to be r=0.98 and is well above the criteria of acceptance (≥0.95). The method gives a linear response and the requirement is fulfilled (see Table 9).

Results—Range

The method is validated in the specific range of $^{227}$Ac content from 0.002% to 0.006% relative to $^{223}$Ra with respect to activity (Bq). Linearity, accuracy, and precision of the method were demonstrated over a range of $^{227}$Ac amounts as listed in Table 16.

TABLE 16

Tested range for linearity, accuracy, and precision of the method

| Validation characteristics | $^{227}$Ac [%] |
|---|---|
| Linearity | 0.003% to 0.006% |
| Accuracy | 0.002% to 0.006% |
| Precision | 0.002%, 0.004%, and 0.006% |

Results—Limit of Quantification and Limit of Detection

A part of a formal validation of the method is to determine limit of detection (LOD) and limit of quantification (LOQ). Limit of blank (LOB) is the highest apparent analyte concentration expected to be found when replicates of a blank sample containing no analyte are tested. LOD is the lowest analyte concentration likely to be reliably distinguished from the LOB and at which detection is feasible. LOQ is the lowest amount one can quantify with sufficiently good (and preselected) accuracy and precision. The γ-peak, 236 keV, which is the most abundant $^{227}$Th peak, is used for quantification of the ingrowth of $^{227}$Th from $^{227}$Ac. The LOD and LOQ were determined as described using the equations:

$$LOD = 2.71 + 3.29\left(B\left(1 + \frac{n}{2m}\right)\right)^{\frac{1}{2}} \quad (5)$$

$$LOQ = 50\left(1 + \left(1 + \frac{nB}{25m}\right)^{\frac{1}{2}}\right) \quad (6)$$

Where:
n=Number of channels in the peak region
m=Number of channels used for the background estimation
B=Background correction Calculated LOD and LOQ from equations 5 and 6 are given in counts and the corresponding activity (Bq) was calculated using the following equation:

$$A_E = \frac{N_E}{\varepsilon_E \cdot t \cdot \gamma} \quad (7)$$

$A_E$: The activity in Bq of a nuclide based on a γ-peak with energy E
$N_E$: the net peak area for a γ-peak at energy E (counts)
$\epsilon_E$: the detector efficiency at energy E
γ: emission probability
t: counting time The LOD was calculated to be 1.8 Bq. This corresponds to 8% of the specification limit as the ingrowth after 24 hours from 100% of specification (600 Bq) corresponds to 22 Bq. The method is suitable to detect an $^{227}$Ac content of 0.0003% (LOD). The LOQ was calculated to 7 Bq of $^{227}$Th this corresponds to 32% of the specification limit. The method is suitable to quantify an $^{227}$Ac content of 0.0013% (LOQ).

A summary of the validation results is presented in Table 17. Accuracy and precision were assessed on drug substance sample solutions spiked with $^{227}$Ac activity ranging from 60 to 140% of the specification limit. 100% of the specification limits corresponds to 0.004% $^{227}$Ac relative to $^{223}$Ra.

TABLE 17

Summary of validation results

| Validation Parameters | | Samples (% of specification) | Acceptance Criteria | Results |
|---|---|---|---|---|
| Accuracy as % recovery (average, n = 11) | | Spiked samples from 60-140% | 70-130% | 92.2% |
| Correlation coefficient, r | | Samples from 78-156% | >0.95 | 0.98 |
| Repeatability (% RSD) | 60% of specification (n = 3) | Spiked samples (60%) | <30% | 25.9% |
| | 100% of specification (n = 3) | Spiked samples (100%) | <30% | 6.4% |
| | 140% of specification (n = 3) | Spiked samples (140%) | <30% | 1.7% |
| LOQ (Bq) | | Spiked samples | NA | 7 |
| LOD (Bq) | | Spiked samples | NA | 2 |

As seen from Table 17, LOD is 2 Bq and LOQ is 7 Bq. This corresponds to approximately 8% and 32% of the specification limit, respectively. Investigation of the specificity shows that the γ-ray energy for quantification of $^{227}$Th from $^{227}$Ac is clearly resolved from interfering γ-ray energies. There are no interferences from the matrix.

All validation parameters met the pre-specified acceptance criteria. The method is considered suitable for its intended use.

The invention claimed is:
1. A method for the quantification of $^{227}$Ac in a $^{223}$Ra composition, said method comprising:
   (i) passing said $^{223}$Ra composition through a first solid phase extraction column A, wherein said column A comprises a thorium specific resin;
   (ii) passing the eluate of column A through a second solid phase extraction column B, wherein said column B comprises an actinium specific resin; and
   (iii) recovering the $^{227}$Ac absorbed onto the resin in column B and determining the amount thereof.
2. A method as claimed in claim 1, wherein the thorium specific resin comprises a phosphonate extractant.
3. A method as claimed in claim 2, wherein the phosphonate extractant is an alkyl phosphonate extractant.
4. A method as claimed in claim 1, wherein the thorium specific resin comprises a dialkyl alkyl phosphonate extractant of Formula I:

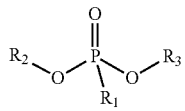

wherein each of $R_1$-$R_3$ is independently a $C_3$-$C_8$ straight or branched chain alkyl group.
5. A method as claimed in claim 4, wherein the dialkyl alkyl phosphonate extractant is a dipentyl pentylphosphonate extractant.
6. A method as claimed in claim 1, wherein the actinium specific resin comprises a diglycolamide extractant.
7. A method as claimed in claim 1, wherein the actinium specific resin comprises a tetra-alkyl diglycolamide extractant of Formula II:

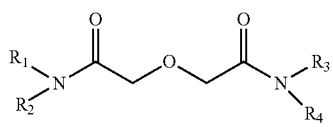

wherein $R_1$-$R_4$ are independently $C_3$-$C_{12}$ straight or branched chain alkyl groups.
8. A method as claimed in claim 7, wherein the tetra-alkyl diglycolamide extractant is a N,N,N',N'-tetra-n-octyldiglycolamide (DGA) extractant.
9. A method as claimed in claim 1, wherein column A and column B are arranged in series.
10. A method as claimed in claim 1, wherein the eluent used in both columns A and B comprises aqueous nitric acid.
11. A method as claimed in claim 1, wherein recovery of the $^{227}$Ac in step (iii) is achieved by washing column B with an aqueous acid.
12. A method as claimed in claim 11, wherein the washing volume of the aqueous acid is 16 to 400 times the volume of column B.
13. A method as claimed in claim 12, wherein the washing volume of the aqueous acid is 40 to 200 times the volume of column B.
14. A method as claimed in claim 1, wherein the determination in step (iii) is achieved by γ-spectrometry via in-growth and detection of the daughter $^{227}$Th.
15. A method as claimed in claim 1, said method comprising:
   (i) Adding a volume of a $^{223}$Ra composition corresponding to a known activity of $^{223}$Ra to an equal volume of nitric acid;
   (ii) Transferring the sample from step (i) to the input of a first solid phase extraction column A comprising a thorium specific resin arranged in series with a second solid phase extraction column B comprising an actinium specific resin;
   (iii) Passing said sample through both columns A and B;
   (iv) Washing both columns with nitric acid in an amount of 20-100 times the combined volumes of the two columns;
   (v) Disconnecting column A from column B;
   (vi) Washing column B with nitric acid in an amount of 40-200 times its volume;
   (vii) Washing column B with nitric acid in an amount of 40-200 times its volume at a concentration less than that used in step (vi); and (viii) Determining the amount of $^{227}$Ac present in the eluate from column B obtained in step (vii).

16. A method as claimed in claim 15, wherein the determination in step (viii) is achieved by γ-spectrometry via in-growth and detection of the daughter $^{227}$Th.

17. A method as claimed in claim 15, wherein the nitric acid in steps (iv) and (vi) is 4 mol/L nitric acid.

18. A method as claimed in claim 15, wherein the nitric acid in step (vii) is 0.05 mol/L nitric acid.

* * * * *